(12) United States Patent
Chun et al.

(10) Patent No.: US 7,951,967 B2
(45) Date of Patent: May 31, 2011

(54) METHOD AND APPARATUS FOR PREPARING FATTY ACID ALKYL ESTER USING FATTY ACID

(75) Inventors: Shin-ho Chun, Seongnam-si (KR); Hyun-Jun Cho, Seoul (KR); Hang-Duk Roh, Ansan-si (KR); Jae-Bong Lim, Anyang-si (KR); Jong-In Lee, Seongnam-si (KR); Chan-Woo Moon, Ulsan (KR); Byung-Hui Kim, Suwon-si (KR)

(73) Assignee: SK Chemicals Co., Ltd., Suwon-si (KR)

( * ) Notice: Subject to any disclaimer, the term of this patent is extended or adjusted under 35 U.S.C. 154(b) by 314 days.

(21) Appl. No.: 12/161,784

(22) PCT Filed: Apr. 28, 2006

(86) PCT No.: PCT/KR2006/001620
§ 371 (c)(1),
(2), (4) Date: Jul. 22, 2008

(87) PCT Pub. No.: WO2007/126166
PCT Pub. Date: Nov. 8, 2007

(65) Prior Publication Data
US 2010/0228042 A1    Sep. 9, 2010

(51) Int. Cl.
*C11C 3/00* (2006.01)
(52) U.S. Cl. .................. 554/162; 422/187; 422/188
(58) Field of Classification Search .................. 554/162; 422/187, 188
See application file for complete search history.

(56) References Cited

U.S. PATENT DOCUMENTS

| 4,164,506 A | 8/1979 | Kawahara et al. |
| 4,608,202 A | 8/1986 | Lepper et al. |
| 4,652,406 A | 3/1987 | Lepper et al. |
| 5,908,946 A | 6/1999 | Stern et al. |

(Continued)

FOREIGN PATENT DOCUMENTS

CN    1247221 A    3/2000

(Continued)

OTHER PUBLICATIONS

Indian Office Action mailed Jan. 18, 2011.

*Primary Examiner* — Deborah D Carr
(74) *Attorney, Agent, or Firm* — Birch, Stewart, Kolasch & Birch, LLP

(57) ABSTRACT

A method and an apparatus for preparing fatty acid alkyl ester for bio-diesels are disclosed, wherein fatty acid, specifically fatty acid distillate reacts with alcohol, without a catalyst. The method does not require the purification process of the catalyst and glycerin, and has the superior conversion ratio of fatty acid. The method for preparing fatty acid alkyl ester for bio-diesel fuels comprises the step of esterifying fatty acid raw material with alcohol, under a temperature of 200 to 350° C. and a pressure of atmospheric pressure to 10 bar. The apparatus for preparing fatty acid alkyl ester for bio-diesel fuels, comprises: the first reactor for esterifying fatty acid raw material with alcohol under a temperature of 200° C. to 350° C. and a pressure of atmospheric pressure to 10 bar and for converting 80 to 90% of total fatty acid into fatty acid alkyl ester; and the second reactor for converting remaining fatty acid unconverted at the first reactor into fatty acid alkyl ester.

12 Claims, 2 Drawing Sheets

U.S. PATENT DOCUMENTS

| | | | |
|---|---|---|---|
| 6,187,939 B1 | 2/2001 | Sasaki et al. | |
| 6,878,837 B2 * | 4/2005 | Bournay et al. | 554/169 |
| 7,256,301 B2 | 8/2007 | Erguen et al. | |
| 2006/0063241 A1 | 3/2006 | Chou | |

FOREIGN PATENT DOCUMENTS

| | | | |
|---|---|---|---|
| EP | 0127104 B1 | | 12/1984 |
| EP | 0184740 B1 | | 6/1986 |
| EP | 0 198 243 A2 | | 10/1986 |
| JP | 2002-294277 A | | 10/2002 |
| JP | 2005-177722 A | | 7/2005 |
| JP | 2005-206575 A | | 8/2005 |
| KR | 10-2004-0087625 A | | 10/2004 |
| KR | 10-2004-0101446 A | | 12/2004 |
| KR | 20050088297 | * | 5/2005 |
| KR | 10-2005-88297 A | | 9/2005 |
| SU | 298357 | * | 12/1984 |
| SU | 298357 A | | 12/1984 |
| WO | 03087278 | * | 10/2003 |
| WO | WO 03/087278 A1 | | 10/2003 |
| WO | WO-2004/048311 A1 | | 6/2004 |
| WO | WO 2005/021697 A1 | | 3/2005 |

* cited by examiner

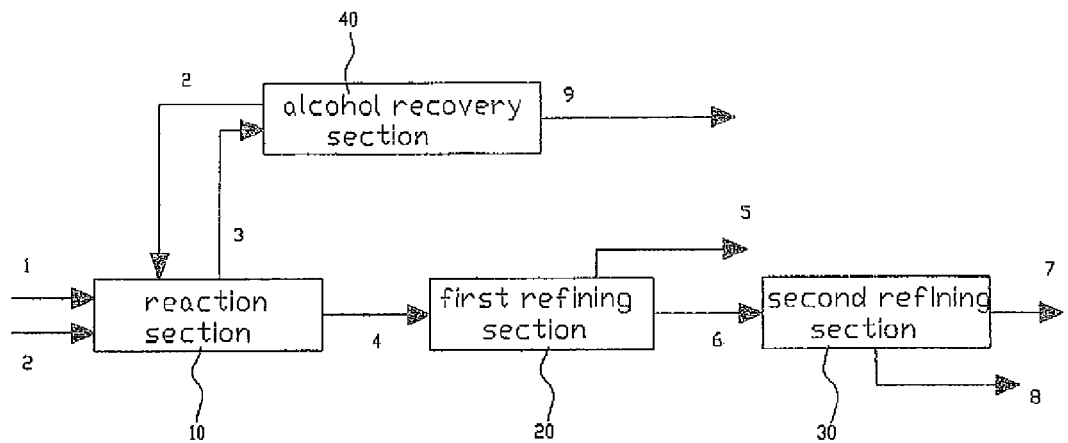
[Fig. 1]
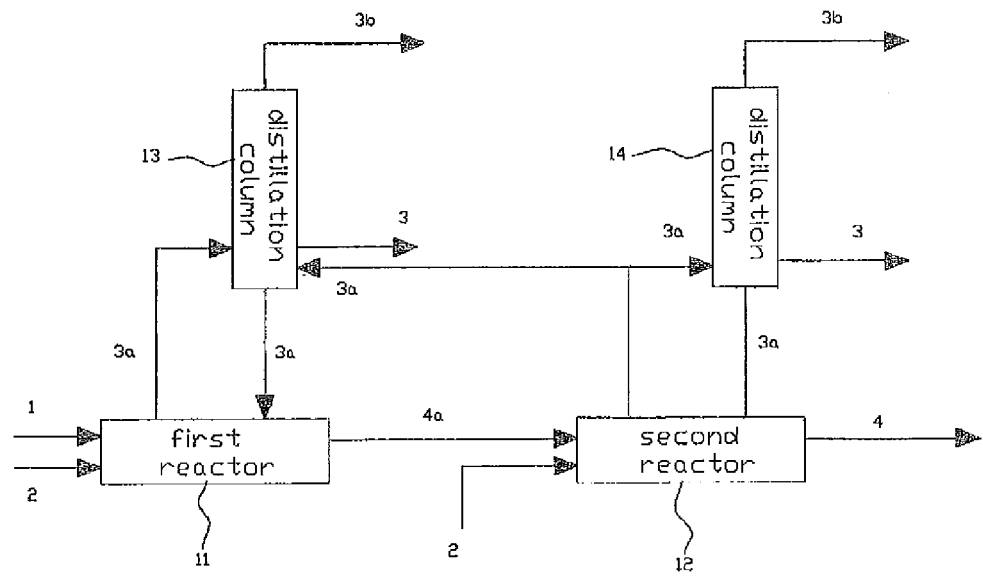
[Fig. 2]
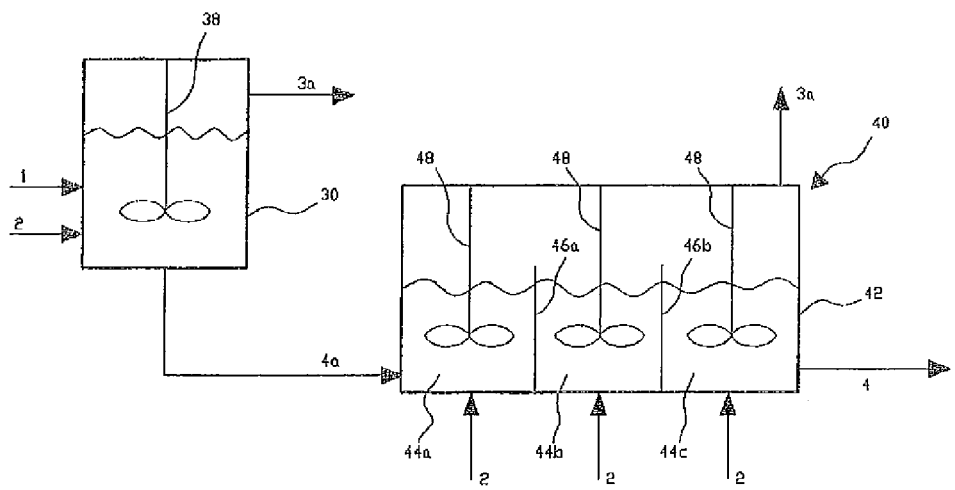
[Fig. 3]

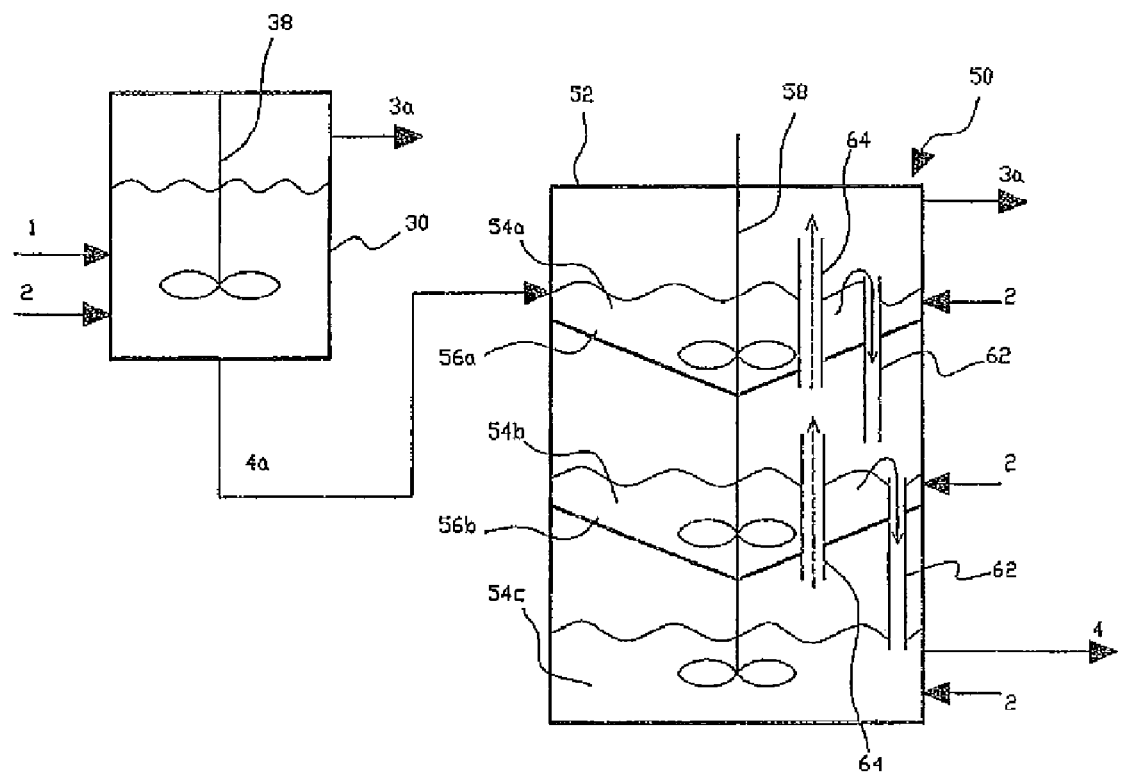
[Fig. 4]

METHOD AND APPARATUS FOR PREPARING FATTY ACID ALKYL ESTER USING FATTY ACID

TECHNICAL FIELD

This invention relates to a method and an apparatus for preparing fatty acid alkyl ester using fatty acid, and more particularly to a method and an apparatus for preparing fatty acid alkyl ester for bio-diesels by reacting fatty acid, specifically fatty acid distillate with alcohol, without introducing a catalyst. The method does not require the purification process for removing the catalyst and glycerine, and has the superior conversion ratio of fatty acid.

BACKGROUND ART

Diesel, among the various fuels derived from crude mineral oils, have advantages such as good fuel efficiency, low cost and low carbon dioxide generation. On the other hand, there is a problem that combustion of diesel produces a large quantity of air pollution, especially particulates matters. In order to solve the problem, various researches have been conducted on alternative fuel which has similar physical property to diesel, and is economically preferable, and also can prevent the air pollution. The bio-diesel has similar physical property to diesel oil, remarkably reduces air pollution, and is naturally recycling energy source. Generally, the bio-diesel is produced by trans-esterification reaction of vegetable oil such as rapeseed oil, soybean oil, sunflower oil, palm oil, etc, animal fats, waste cooking oil, and so on with alcohol in the presence of acid catalyst or alkali catalyst. In the production of the bio-diesel, about 10 weight % of glycerin with respect to the total amount of bio-diesel is produced as a by-product. Recently, since the plant construction for bio-diesel is rapidly and world-widely progressed, an oversupply of glycerin is expected.

On the other hand, oils and fats generally contain free fatty acids, which exist in the mixed form with triglyceride of fatty acid. The free fatty acids are separated as the by-product in the refining process of oils and fats. Several methods for preparing fatty acid alkyl ester from the separated free fatty acids have been known. The methods for esterification of the free fatty acids are disclosed in European patent publication No. 127104A, European patent publication No. 184740A and U.S. Pat. No. 4,164,506, and so on. In the methods, the esterification reaction is carried out by heating the mixture of fatty acid and fatty acid triglyceride with methanol at about 65° C. in the presence of sulfuric acid or sulfonic acid catalyst. European patent publication No. 708813A discloses the method for increasing the yield of the fatty acid alkyl ester from oils and fats. In the method, the free fatty acid is separated from glycerin phase which is the product of transesterification reaction, and then the separated free fatty acid is esterified. In this method, the free fatty acid is obtained by the neutralization of glycerin phase, and the obtained free fatty acid is reacted for 2 hours at about 85° C. in the presence of strong sulfuric acid catalyst, which reduces the amount of fatty acid from 50% to 12%. In addition, a method for improving esterification reaction efficiency of fatty acid is disclosed (Korean patent unexamined-publication No. 2004-0101446, International Publication No. WO 2003/087278), which utilizes a mechanical apparatus or supersonic waves for causing dynamic turbulence in a reactor. In this method, the esterification is carried out by reacting the fatty acid and/or fatty acid contained in oils and fats with alcohol at a high pressure and a high temperature using sulfuric acid or ion exchange resin as catalyst. Further, Korean patent unexamined-publication No. 2004-87625 discloses a method for removing free fatty acid from waste cooking oil, using solid acid catalyst. The above mentioned methods commonly use an acid catalyst, such as sulfuric acid etc. If such an acid catalyst is not completely removed after the reaction, the quality of bio-diesel is deteriorated. Therefore, complicate processes for neutralizing, filtering, washing and cleaning the acid catalyst must be needed. Also the lifecycle of the solid acid catalyst is not long and cost for recycling the same is expensive. Furthermore, in the above-mentioned conventional methods, since the esterification of fatty acid is carried out at low temperature, water produced during the reaction is not efficiently removed to outside of the reaction system. Thus, the conversion ratio of fatty acid into fatty acid alkyl ester is low, and the physical properties of the obtained fatty acid alkyl ester are not suitable for bio-diesel.

DISCLOSURE OF INVENTION

Technical Problem

Therefore, it is an object of the present invention to provide a method for preparing fatty acid alkyl ester suitable for bio-diesel fuel.

It is other object of the present invention to provide a method for preparing fatty acid alkyl ester by esterifying fatty acid with alcohol at high temperature range without using catalyst, which is different from the conventional method for preparing fatty acid alkyl ester and glycerin by carrying out the transesterification reaction of vegetable oils or animal fats with alcohol in the presence of catalyst.

It is another object of the present invention to provide a method for conveniently and economically preparing fatty acid alkyl ester without producing glycerin, by using fatty acid distillate as a raw material, which is generated as a by-product during the refining process of vegetable oils.

It is still another object of the present invention to provide an apparatus for efficiently carrying out the preparation of fatty acid alkyl ester.

Technical Solution

To achieve these and other objects, the present invention provides the method for preparing fatty acid alkyl ester for bio-diesel fuels, which comprises the step of esterifying fatty acid raw material with alcohol, under a temperature of 200 to 350° C. and a pressure of atmospheric pressure to 10 bar. The present invention also provides the apparatus for preparing fatty acid alkyl ester for bio-diesel fuels under a temperature of 200° C. to 350° C. and a pressure of atmospheric pressure to 10 bar, which comprises: the first reactor for esterifying fatty acid of raw material with alcohol, in which 80 to 90% of total fatty acid is converted into fatty acid alkyl ester; and the second reactor for converting remaining fatty acid unconverted at the first reactor into fatty acid alkyl ester. The present invention also provides the apparatus for preparing fatty acid alkyl ester for bio-diesel fuels, which comprises: a reacting section having at least one reactor, for reacting fatty acid raw material with alcohol to produce crude fatty acid alkyl ester; the first refining section for removing impurities having low boiling point from the fatty acid alkyl ester by distillation to produce a firstly refined fatty acid alkyl ester; and the second refining section for the distillation of the firstly refined fatty acid alkyl ester to obtain fatty acid alkyl ester and removing residues, wherein an alcohol recovery section is connected to the top of the reacting section, for recycling an excess alcohol and removing water produced at the reacting section.

A more complete appreciation of the invention, and many of the attendant advantages thereof, will be better appreciated with reference to the following detailed description and the accompanying drawings.

FIG. 1 shows the entire configuration of the apparatus for preparing fatty acid alkyl ester according to an embodiment of the present invention. As shown in FIG. 1, fatty acid raw material (1, hereinafter, if necessary, simply "fatty acid") and alcohol (2) are introduced into a reaction section (10) and then esterification reaction is carried out under a constant temperature and pressure. The crude fatty acid alkyl ester (4) produced at the esterification reaction is transferred to the first refining section (20), and the impurities (5) having low boiling point can be removed through top of distillation column of the first refining section (20) by distillation. The firstly refined fatty acid alkyl ester (6) is transferred to the second refining section (30), and distilled to leave residues (residual impurities, 8) in the second refining section (30) and to exhaust or discharge the secondly refined fatty acid alkyl ester (7) through the top of distillation column of the second refining section (30). On the other hand, the reaction section (10) is connected to an alcohol recovery section (40) so that a mixture (alcohol/water, 3) of water produced at the reaction section (10) and excess alcohol which is unreacted at the reaction section (10), is introduced into the alcohol recovery section (40). In the alcohol recovery section (40), the alcohol (2) is distilled and recycled to the reaction section (10) and water (9) is transferred to a waste water disposal plant.

In the present invention, as the fatty acid raw material (1) for preparing fatty acid alkyl ester (7), pure fatty acid (RCOOH) in which carbon atom number of aliphatic part (R) is 14 to 24, can be used. However, it is preferable to use fatty acid distillate as the raw material. The fatty acid distillate is produced as a by-product during the process of refining crude vegetable oil collected from vegetables such as rapeseed, soybean, sunflower, palm, or so on, to obtain refined vegetable oil, such as rapeseed oil, soybean oil, sunflower oil or palm oil, or so on. As occasion demands, a mixture of the pure fatty acid and the fatty acid distillate can be used. The fatty acid distillate generally contains 65 to 95 weight %, preferably 80 to 85 weight % of the fatty acid in which carbon atom number of aliphatic part (R) is 14 to 24. The remaining components of the fatty acid distillate include β_carotin, fatty acid in which carbon atom number of aliphatic part (R) is less than 14 or more than 24, and so on. In the method for preparing fatty acid alkyl ester according to the present invention, it is economically advantageous to use the fatty acid distillate as the raw material. As the alcohol for the present invention, monovalent alcohols having 1 to 10 carbon atoms, preferably monovalent alcohols having 1 to 4 of carbon atom such as methanol, ethanol, propanol, or so on, and more preferably methanol, can be used.

In the present invention, the esterification reaction can be carried out in one-step or two-steps. In the one-step esterification reaction, the reaction section (10) is constituted by one reactor and one distillation column. In the two-step esterification reaction, the reaction section (10) may be constituted by two reactors and one distillation column where the one distillation column is commonly used, or one reactor and one distillation column can be used each step as shown in FIG. 2. Moreover, the reactor and the distillation column may not be separated, but can be integrated, wherein the lower part of the integrated apparatus works as the reactor, and the upper part of the integrated apparatus works as the distillation column. In this case, a seal tray can be installed between the upper part for the distillation column and the lower part for the reactor to prevent water from falling from the upper part to the lower part. The esterification reaction according to the present invention can be carried out by a batch process or a continuous process, and carried out by one-step or two-steps as previously described. In the continuous process, if the retention (stay) time is sufficient, the one-step reaction can provide a sufficiently high conversion ratio, however it is preferable to carry out the two-step reaction. In case of the batch process, if the conversion ratio of the first reaction is insufficient, the conversion ratio can be improved by carrying out the second reaction with modified reaction conditions.

FIG. 2 shows an embodiment of the reaction section (10) in FIG. 1, which is constituted by two reactors (11, 12) and two distillation columns (13, 14). Referring to FIG. 2, a product (4a) which is obtained by the reaction in the first reactor (11) is introduced into the second reactor (12) together with alcohol (2) for the second reaction in the second reactor (12). The crude fatty acid alkyl ester (4) which is the product of the second reaction in the second reactor (12) is transferred the refining sections (20, 30) in FIG. 1. The mixtures (3a) containing water produced at each reactor (11, 12) and the excess alcohol which is unreacted are exhausted into the distillation columns (13, 14), respectively. The mixture (3a) is separated in the distillation columns (13, 14) so that pure alcohol or the azeotrope of alcohol/water (3b) is exhausted via the upper part of the distillation columns (13, 14) and the mixture (3) containing alcohol and water, in which the concentration of water is high, is exhausted through the lower part of the distillation columns (13, 14). Here, the pure alcohol or the azeotrope of alcohol/water (3b) obtained at the upper part of the distillation columns (13, 14) can be reused as an alcohol which is introduced into the reaction section (10). The alcohol/water mixture (3), in which the concentration of water is high, is transferred to the alcohol recovery section (40) of FIG. 1.

Hereinafter, the preparation conditions of fatty acid alkyl ester according to the present invention will be described in detail. The catalyst is not introduced in the esterification reaction of the present invention. The esterification reaction of the present invention is carried out at high temperature. Thus, high reaction rate and high conversion ratio of fatty acid into fatty acid alkyl ester can be obtained. The temperature for the esterification reaction of the present invention is 200 to 350° C., preferably 250 to 320° C. The pressure for the esterification reaction of the present invention is atmospheric pressure to 10 bar, preferably atmospheric pressure to 5 bar. The esterification reaction according to the present invention can be carried out by the batch process or the continuous process. In case of the batch process, the esterification reaction may be performed while maintaining the constant pressure of atmospheric pressure to 10 bar. Alternatively, the initial esterification reaction is carried out at a relatively high pressure of 3 bar to 10 bar to increase the reaction rate, and then the latter esterification reaction is carried out at a relatively low pressure of atmospheric pressure to 3 bar to remove the produced water from the reactant, thereby enhancing the conversion ratio of the reaction. In case of the continuous process, the pressure in all reaction procedure may be the constant pressure of atmospheric pressure to 10 bar, or the first reactor of the two-step reaction is maintained at a pressure of 3 bar to 10 bar and the second reactor of the two-step reaction is maintained at a pressure of atmospheric pressure to 3 bar. If the reaction temperature and the reaction pressure deviate from the above-mentioned ranges, the reaction rate and the conversion ratio of fatty acid are reduced or adverse side reactions may occur.

Since the conventional esterification reaction of fatty acid using catalyst is carried out at low temperature of less than 100° C. and water produced during the esterifiaction reaction cannot be removed from the reaction system, the esterification reaction cannot be progressed beyond the reaction equilibrium. However, the esterification reaction of the present invention is performed at high temperature of 200 to 350° C., so water produced during the esterifiaction reaction can be continuously removed from the reaction system together with excess alcohol. Accordingly, the esterification reaction according to the present invention is progressed beyond the reaction equilibrium so that the conversion ratio of fatty acid is excellent near to the complete reaction. Specifically, in order to use the fatty acid alkyl ester as the bio-diesel, total acid number (mg KOH/g) of the fatty acid alkyl ester should be less than a predetermined value. However, if the unreacted fatty acid component remains, the total acid number (mg KOH/g) of the produced fatty acid alkyl ester becomes high, and the fatty acid alkyl ester cannot satisfy the quality criteria for the bio-diesel. Since the unreacted fatty acid component have similar boiling point with fatty acid methyl ester, it is very difficult for the unreacted fatty acid component to be separated by the distillation. Thus, the unreacted fatty acid component should be prevented by the complete esterification reaction. The method for preparing fatty acid alkyl ester according to the present invention shows more than 99.7% of the conversion ratio of fatty acid into fatty acid alkyl ester, which satisfy the total acid number quality criteria for the biodiesel. On the other hands, with the conventional method for preparing fatty acid alkyl ester using catalyst, it is difficult to increase the conversion ratio of fatty acid to be more than 99.7%.

In the continuous process, alcohol is introduced by an amount of about 0.5 to 5 times by weight, preferably 1 to 3 times by weight, with respect to the introduced amount of fatty acid. The retention time of the total reaction process is 1 to 10 hours, preferably 3 to 5 hours. If the introduced amount of alcohol deviates from the above-mentioned range, the reaction rate and the reaction yield can be reduced and it is economically undesirable. In the batch process, fatty acid and alcohol are initially introduced into a reactor, wherein the amount of alcohol is 0.1 to 3 times by weight with respect to amount of fatty acid. When the temperature and pressure of the reactor reaches predetermined temperature and pressure, alcohol for inducing main reaction is introduced into the reactor. In this case, the total amount of alcohol to be introduced during the total reaction time is 0.5 to 5 times by weight, preferably 1 to 3 times by weight with respect to the amount of fatty acid. The reaction time is 1 to 10 hours, preferably 3 to 5 hours. Also, at the latter (second half) period of the reaction of the continuous process or the batch process, if the introduced amount of alcohol increases by 1 to 3 times, preferably 1.5 to 3 times with respect to the initial introduced amount of alcohol, the reaction conversion ratio can be further improved.

The exemplary esterification reactor of the present invention includes a continuous stirred tank reactor (CSTR type) on which a stirrer is installed, a plug flow reactor (PFR) in which a baffle is mounted for providing a sufficient retention time, or so on. In a preferable reactor, at least one comparting wall is installed in the reactor to divide the interior of the reactor into several compartments. Reactants consecutively overflow the comparting wall to be consecutively transferred to the adjacent compartment, which provides sufficient retention time.

FIG. 3 and FIG. 4 show preferable embodiments of the reactor which can be used as the apparatus for preparing fatty acid alkyl ester according to the present invention. As shown in FIG. 3, the esterification reactor for the present invention includes the first reactor (30) for converting 80 to 90% of the total fatty acid to fatty acid alkyl ester and the second reactor (40) for converting the remaining fatty acid which is not converted in the first reactor (30) to fatty acid alkyl ester. The raw materials, fatty acid (1) and alcohol (2) are introduced into the first reactor (30) for the first reaction. The product (4a) of the first reaction is extracted through the lower part of the first reactor (30) and the mixture (3a) containing water produced at the first reaction and the excess alcohol which is unreacted at the first reaction, is extracted in gas phase through the upper part of the first reactor (30). The second reactor (40) includes a reactor body (42) and at least one comparting wall (46a, 46b). The comparting walls (46a, 46b) divide the interior of the reactor (40) into two or more compartments (44a, 44b, 44c), wherein the upper parts of the comparting walls (46a, 46b) are open so that the reactants overflow over the comparting walls (46a, 46b). The divided compartments (44a, 44b, 44c) of the second reactor (40) can be formed on the same plane and the adjacent compartments (44a, 44b, 44c) can be liquid flowably connected to each other via the upper part of the comparting walls (46a, 46b). Accordingly, when the product (4a) of the first reaction and alcohol (2) are introduced into the first compartment (44a), and sufficiently react in the first compartment (44a). As the introduced amount of the product (4a) increases, the product (4a) flows into the second compartment (46b) over the first comparting wall (44a). In the second compartment (44b), the product (4a) again reacts with alcohol (2) and then overflows into the third compartment (44c) over the second comparting wall (46b). In the third compartment (44c), the product (4a) reacts again with alcohol (2) and is converted into crude fatty acid alkyl ester (4). Then the crude fatty acid alkyl ester (4) is extracted from the second reactor (40). At this time, the mixture (3a) containing water produced during the reaction and alcohol is exhausted via the upper part of the second reactor (40). In addition, stirrers (38, 48) for stirring the reactants may be installed in the first reactor (30) and in the compartments (44a, 44b, 44c) of the second reactor (40).

The esterification reactor shown in FIG. 4 includes the first reactor (30) for converting 80 to 90% of the total fatty acid to fatty acid alkyl ester and the second reactor (50) for converting remaining fatty acid which is not converted in the first reactor (30) to fatty acid alkyl ester. The first reactor (30) has the same structure described in FIG. 3. The second reactor (50) includes a reactor body (52) and at least one comparting wall (56a, 56b). The comparting walls (56a, 56b) divide the interior of the second reactor (50) into two or more compartments (54a, 54b, 54c). The compartments (54a, 54b, 54c) in the second reactor (50) are arranged in the form of vertical stack, and the comparting walls (56a, 56b) form the bottom plates of the compartments (54a, 54b). Namely, the first compartment (54a) and the second compartment (54b), which is located under the first compartment (54a), are divided by the first comparting wall (56a). A liquid guide path (62) and a gas guide path (64) are installed on the first comparting wall (56a). The liquid guide path (62) and the gas guide path (64) penetrate the first comparting wall (56a). One end of the liquid guide path (62) is located at the height corresponding to the surface of reactants located in the first compartment (56a), and the other end of the liquid guide path (62) is located at the height which is higher than the surface of reactants located in the second compartment (54b). One end of the gas guide path (64) is located at the height which is higher than the surface of reactant located in the first compartment (54a), and the other end of the gas guide path (64) is located at the height which is higher than the surface of reactant located in the second compartment (54b). The liquid guide path (62) and the gas guide path (64) are installed on each comparting walls (56a, 56b) in the above described manner. Thus, the vertically adjacent compartments (54a, 54b, 54c) are communicated with each other via the liquid guide path (62) and the gas guide path (64) installed on the comparting walls (56a, 56b). As a result, the product (4a) of the first reaction and alcohol (2) are introduced into the first compartment (54a), and sufficiently react in the first compartment (54a). As the introduced amount of the product (4a) of the first reaction increases, the product of first compartment (54a) overflows via the liquid guide path (62) into the second compartment (54b) to react with alcohol (2) introduced into the second compartment (54b) and again overflows into the third compartment (54c) via the liquid guide path (62) installed on the second comparting wall (56b). In the third compartment (54c), the product of second compartment (54b) reacts with alcohol (2) and is converted into crude fatty acid alkyl ester (4). The crude fatty acid alkyl ester (4) is extracted from the second reactor (50). At this time, the mixture (3a) containing water produced during the reaction and excess alcohol sequentially moves to the upper compartments (54b, 54a) via the gas guide path (64), and finally exhausted from the second reactor (50) through the upper part of the first compartment (54a).

As described above, in the present invention, 80 to 90% of the total fatty acid is converted to fatty acid alkyl ester in the first reactor (30), and remaining unconverted fatty acid is converted to fatty acid alkyl ester in the second reactor (40, 50) while sequentially passing the adjacent compartments of the second reactor (40, 50). Thus, the retention time of the fatty acid can be prolonged, and the conversion ratio of fatty acid into fatty acid alkyl ester (conversion reaction efficiency) can be improved.

The most part of the crude fatty acid alkyl ester (4) obtained by esterification reaction of the present invention is fatty acid alkyl ester. However, in order to use the fatty acid alkyl ester of the present invention as industrial fuels or bio-diesel fuels, low molecular weight fatty acid alkyl esters, high molecular weight fatty acid alkyl esters, residues, and so on should be removed from the crude fatty acid alkyl ester (4). Especially for fatty acid methyl ester, fatty acid alkyl ester having carbon atom number of aliphatic part being less than 14 or more than 24 and other low molecular weight impurities should be removed, so as to satisfy the quality criteria of the bio-diesel. Therefore, in the present invention, the crude fatty acid alkyl ester (4) is refined by the two-step distillation process. Referring to FIG. 1, in the first refining section (20) of the present invention, 1 to 10 weight %, preferably 2 to 5 weight % of an introduced amount (feed) is removed through the upper part of a distillation column by maintaining the temperature of the lower part of the distillation column to be 150 to 250° C., preferably 180 to 220° C. at the vacuum condition of 0.1 to 150 torr, preferably 0.1 to 40 torr. When the amount removed through the upper part of the distillation column is less than 1 weight % of the feed, impurities having low boiling point cannot be sufficiently removed. When amount removed through the upper part of the distillation column is more than 10 weight % of the feed, the distillation yield may be reduced. In this case, most of the impurities of low boiling point which are removed through the upper part of the distillation column are low molecular weight fatty acid alkyl ester. Thus, the removed impurities can be directly used as fuels for boilers, etc, without additional process. In the second refining section (30) of the present invention, the impurities of 1 to 25 weight % of an introduced feed are left for removal in the lower part of the distillation column, and the refined fatty acid alkyl ester of high purity is extracted through the upper part of the distillation column by maintaining the temperature of the lower part of the distillation column to be 200 to 300° C., preferably 220 to 280° C. at the vacuum condition of 0.1 to 150 torr, preferably 0.1 to 40 torr. The amount of the removed impurities (residue) can be varied according to the composition of the fatty acid raw material. However, when the amount remaining on the lower part of the distillation column is less than 1 weight % of the feed, the purity of fatty acid alkyl ester can be deteriorated. When the amount remaining on the lower part of the distillation column is more than 25 weight % of the feed, the distillation yield may be reduced. Here, most of the remaining impurities are fatty acid alkyl ester having carbon atom number of aliphatic part being more than 24. Thus, the remaining impurities can be used as fuels for boilers, etc. The fatty acid alkyl ester refined by the above-mentioned method, specifically fatty acid methyl ester satisfies all quality criteria on the biodiesels in this country and foreign major countries including U.S.A. and Europe. Therefore, the fatty acid alkyl ester of the present invention can be directly used as biodiesel.

On the other hand, water produced during the esterification reaction of the present invention is extracted from the reaction section (10) together with excess alcohol which is unreacted in the esterification reaction, and the mixture is separated at the alcohol recovery section (40). After separation, water is transferred to the waste water disposal plant, and the alcohol is recycled to the reaction section (10) for reuse. The alcohol recovery section (40) includes a distillation column and affiliated facilities therefor. The temperature of the lower part of the distillation column of the alcohol recovery section (40) is controlled according to the boiling point of alcohol so as to distil alcohol. The distilled and reused alcohol can contain 0 to 10 weight %, specifically 0.001 to 10 weight % of water. If the amount of water contained in alcohol is more than 10 weight %, the esterification rate in the reaction section (10) may be reduced. Also, in case of using methanol, by only using single distillation column, methanol can be refined with sufficiently high purity and can be recycled to the reaction section (10). In case of using alcohol having at least 2 carbon atoms, for example, ethanol, the alcohol/water azeotrope is extracted from the distillation column of the alcohol recovery section (40), is subject to dehydration process to remove water and then the water removed alcohol is recycled to the reaction section (10).

Hereinafter, the preferable examples are provided for better understanding of the present invention. However, the present invention is not limited to the following examples.

EXAMPLE 1

Preparation of Fatty Acid Methyl Ester (Continuous Process)

The esterification reaction was carried out by two-step reaction using the reactors of FIG. 3. Firstly, the first reactor was controlled to temperature of 300° C. and pressure of 3 bar. 1 kg of fatty acid distillate, which is obtained by distilling crude palm oil, and 1 kg of methanol were introduced into the reactor and the reaction was carried out for 2 hours. Then, the temperature of the second reactor was maintained to be same with that of the first reactor, and the pressure was reduced to atmospheric pressure, and the reaction in the second reactor was carried out for 2 hours. For the reaction in the second reactor, 2 kg of methanol (two times of the first feed amount) was divided by 3, and each divided part was introduced into each compartment (44a, 44b, 44c). The reaction product was transferred to the first refining section. In the first refining section, the lower part of the distillation column was maintained at 200° C. and 20 torr, and the impurities having low boiling point of 3 weight % of the introduced feed was removed by distillation through the upper part of the distillation column. The firstly refined product was transferred to the second refining section. In the second refining section, the lower part of the distillation column was maintained at 250° C. and 20 torr, and fatty acid methyl ester of 80 weight % of the introduced feed was obtained by distillation. On the other hand, the water produced in the reaction section and the unreacted methanol was transferred to the alcohol recovery section, and methanol was recovered by distillation, and the recovered methanol was recycled and reused. The conversion ratio for fatty acid methyl ester by the above mentioned method was 99.7%.

EXAMPLE 2

Preparation of Fatty Acid Methyl Ester (Batch Process)

The esterification reaction was carried out by one-step reaction using a batch reactor. Firstly, 1 kg of fatty acid distillate and 0.5 kg of methanol were introduced into the reactor. The reactor was controlled to temperature of 300° C. and pressure of 3 bar, and 1 kg of methanol was further added to the reactor, and the reaction was carried out for 2 hours. Thereafter, the pressure of the reactor was reduced to atmospheric pressure, and the reaction was further carried out for 1 hour, while introducing 2 kg of methanol (two times of the first feed amount). The reaction product was refined according to the method and conditions of Example 1, and fatty acid alkyl methyl ester of 90 weight % of the feed for the second refining step was obtained. On the other hand, the unreacted excess methanol was recovered and reused according to the method of Example 1, and water was removed. The conversion ratio for fatty acid methyl ester by the above mentioned method was 99.8%.

Advantageous Effects

As described above, in the method for preparing fatty acid alkyl ester according to the present invention, fatty acid and alcohol reacts under high temperature and high pressure, without catalyst. Therefore, the neutralizing, filtering, washing and cleaning processes for removing the catalyst are not required. In the present invention, fatty acid alkyl ester of high purity can be obtained by just two-step distillation processes, and thus the total process for producing fatty acid alkyl ester is simplified and cost for process facilities and the operation thereof is reduced. In addition, the present invention is economically favorable since worthless fatty acid distillate and/or cheap fatty acid are used as the raw material. In the present invention, the by-product, such as glycerin is not produced, and excess alcohol can be recoverd and reused. The method for preparing the fatty acid alkyl ester according to the present invention can be applicable to the manufacturing apparatus of an industrial scale as well as of a small scale. Especially, the fatty acid methyl ester prepared according to the present invention can be directly used as the bio-diesel without additional process.

BRIEF DESCRIPTION OF THE DRAWINGS

FIG. 1 is a drawing for showing the entire configuration of the apparatus for preparing fatty acid alkyl ester according to an embodiment of the present invention.

FIG. 2 is a drawing for showing an embodiment of the reaction section in FIG. 1.

FIG. 3 and FIG. 4 are drawings for showing embodiments of the reactor which can be used for an apparatus for preparing fatty acid alkyl ester according to the present invention.

The invention claimed is:

1. A method for preparing fatty acid alkyl ester for bio-diesel fuels, comprising the step of esterifying fatty acid raw material with alcohol without a catalyst, under a temperature of 200 to 350° C. and a pressure of atmospheric pressure to 10 bar so that water produced during the esterification reaction can be continuously removed together with excess alcohol.

2. The method for preparing fatty acid alkyl ester for bio-diesel fuels of claim 1, wherein the fatty acid raw material, which reacts with alcohol, is fatty acid distillate which is produced as a by-product during the process of refining crude vegetable oil to obtain refined vegetable oil.

3. The method or preparing fatty acid alkyl ester for bio-diesel fuels of claim 2, wherein the fatty acid distillate contains 65 to 95 weight % of fatty acid which has carbon atom number of aliphatic part of 14 to 24.

4. The method for preparing fatty acid alkyl ester for bio-diesel fuels of claim 1, further comprising the steps of: firstly refining a crude fatty acid alkyl ester produced at the esterifying step of fatty acid with alcohol, by feeding the crude fatty acid alkyl ester to a distillation column and then distilling impurities having low boiling point from the crude fatty acid alkyl ester, by maintaining the temperature of the lower part of the distillation column to be 150 to 250° C. at the vacuum condition of 0.1 to 150 ton; and secondly refining the firstly refined fatty acid alkyl ester by feeding the firstly refined fatty acid alkyl ester to a distillation column, by maintaining the temperature of the lower part of the distillation column to be 200 to 300° C. at the vacuum condition of 0.1 to 150 ton for obtaining fatty acid which has 14 to 24 of carbon atom number of aliphatic part by distillation and removing residues.

5. The method for preparing fatty acid alkyl ester for bio-diesel fuels of claim 1, wherein the alcohol is introduced by an amount of 0.5 to 5 times by weight with respect to the introduced amount of the fatty acid raw material, the reaction temperature for the esterifying step is 250 to 320° C., and the reaction pressure for the esterifying step is atmospheric pressure to 5 bar.

6. The method for preparing fatty acid alkyl ester for bio-diesel fuels of claim 1, wherein excess alcohol which is unreacted at the esterifying step is extracted through the upper part of a reactor with water produced during the esterifying step, and is introduced into an alcohol recovery section installed outside of the reactor, and is then recycled to the reactor by distillation.

7. An apparatus for preparing fatty acid alkyl ester for bio-diesel fuels, the apparatus comprising:
a first reactor for esterifying fatty acid raw material with alcohol without using catalyst under a temperature of 200° C. to 350° C. and a pressure of atmospheric pressure to 10 bar and for converting 80 to 90% of total fatty acid into fatty acid alkyl ester; and
a second reactor for converting remaining fatty acid unconverted at the first reactor into fatty acid alkyl ester without using catalyst,
wherein a mixture containing water produced at the first reactor and the excess alcohol which is unreacted at the first reactor is extracted in gas phase through the upper part of the first reactor.

8. The apparatus for preparing fatty acid alkyl ester for bio-diesel fuels of claim 7, wherein the second reactor comprises: a reactor body; and at least one comparting wall which divides the interior of the reactor body into two or more compartments, and the upper part of the comparting wall is open so that reactants overflow over the comparting wall.

9. The apparatus for preparing fatty acid alkyl ester for bio-diesel fuels of claim 7, wherein the second reactor comprises: a reactor body; and at least one comparting wall which divides the interior of the reactor body into two or more compartments, the divided compartments in the second reactor are arranged in the form of vertical stack, and a liquid guide path and a gas guide path are installed on the comparting wall.

10. The apparatus for preparing fatty acid alkyl ester for bio-diesel fuels of claim 9, wherein the compartments includes a first compartment and a second compartment which is located under the first compartment, the liquid guide path and the gas guide path penetrate the comparting wall, one end of the liquid guide path is located at the height corresponding to the surface of reactants located in the first compartment, and the other end of the liquid guide path is located at the height which is higher than the surface of reactants located in the second compartment, one end of the gas guide path is located at the height which is higher than the surface of reactant located in the first compartment, and the other end of the gas guide path is located at the height which is higher than the surface of reactant located in the second compartment.

11. An apparatus for preparing fatty acid alkyl ester for bio-diesel fuels, the apparatus comprising: a reacting section having at least one reactor, for reacting fatty acid raw material with alcohol to produce crude fatty acid alkyl ester; a first refining section for removing impurities having low boiling point from the fatty acid alkyl ester by distillation to produce a firstly refined fatty acid alkyl ester; and a second refining section for the distillation of the firstly refined fatty acid alkyl ester to obtain fatty acid alkyl ester and removing residues, wherein an alcohol recovery section is connected to the top of the reacting section, for recycling an excess alcohol and removing water produced at the reacting section.

12. The apparatus for preparing fatty acid alkyl ester for bio-diesel fuels of claim 11, wherein the reactor is a continuous stirred tank reactor on which a stirrer is installed, or a plug flow reactor in which a baffle is mounted.

* * * * *